US011464938B2

(12) United States Patent
Genereux et al.

(10) Patent No.: US 11,464,938 B2
(45) Date of Patent: Oct. 11, 2022

(54) AUDIO TONE PROGRAMMED HYGIENIC AND THERAPEUTIC SLEEP AND WAKE EYE MASK HAVING REMOTELY CONTROLLED SUNRISE AND SUNSET MULTIMODES

(71) Applicant: Headwaters Research & Development Inc, Ottawa (CA)

(72) Inventors: Philippe J Genereux, Ottawa (CA); Rudy A Vandenbelt, Ottawa (CA); Troy G Anderson, Marblehead, MA (US); Adam T Clarke, Ottawa (CA)

(73) Assignee: Headwaters, Inc., Marblehead, MA (US)

( * ) Notice: Subject to any disclaimer, the term of this patent is extended or adjusted under 35 U.S.C. 154(b) by 332 days.

(21) Appl. No.: 16/601,494

(22) Filed: Oct. 14, 2019

(65) Prior Publication Data

US 2020/0038624 A1    Feb. 6, 2020

Related U.S. Application Data

(62) Division of application No. 15/447,191, filed on Mar. 2, 2017, now Pat. No. 10,449,326.

(60) Provisional application No. 62/302,858, filed on Mar. 3, 2016.

(51) Int. Cl.
*A61M 21/02*     (2006.01)
*A61F 9/04*      (2006.01)
*A61M 21/00*     (2006.01)

(52) U.S. Cl.
CPC .............. *A61M 21/02* (2013.01); *A61F 9/04* (2013.01); *A61F 9/045* (2013.01); *A61M 2021/0027* (2013.01); *A61M 2021/0044* (2013.01); *A61M 2021/0083* (2013.01); *A61M 2205/50* (2013.01); *A61M 2205/502* (2013.01); *A61M 2205/8206* (2013.01)

(58) Field of Classification Search
CPC ........ A61M 21/00–02; A61F 9/02–029; A61F 9/04–045; A61F 13/124
See application file for complete search history.

(56) References Cited

U.S. PATENT DOCUMENTS

| 2012/0137406 A1* | 6/2012 | Hide ........................ A61F 9/04 2/206 |
| 2013/0184516 A1* | 7/2013 | Genereux ............ A61N 5/0618 600/28 |
| 2017/0274222 A1* | 9/2017 | Geyer .................. A61N 5/0618 |

FOREIGN PATENT DOCUMENTS

WO    WO-2010035200 A1 *  4/2010 ............. H05B 47/16

* cited by examiner

*Primary Examiner* — Thaddeus B Cox
(74) *Attorney, Agent, or Firm* — Albert Peter Durigon

(57) ABSTRACT

An eye mask for use to wake up and/or to go to sleep provides ease of cleaning or replacement without damaging electrical or optical components; different user selectable sunrise and sunset illumination modes respectively having blue-shifted and red-shifted spectra simulating natural sunrises and sunsets to assimilate the sleep/wake cycle to the natural rhythms of day and night; sunset and/or sunrise illumination modes that oscillate with fixed period or sequentially changing periods that correspond to brainwave frequencies that respectively facilitate going to sleep and/or waking and synergistically co-operate with corresponding sunset or sunrise light fields to help the user to fall into restful sleep or to awake refreshed and alert; and audio tone programming of illumination mode and treatment time and/ or duration of therapy by a remote tone control generator.

4 Claims, 8 Drawing Sheets

AUDIO TONE PROGRAMMED HYGIENIC AND THERAPEUTIC SLEEP AND WAKE EYE MASK HAVING REMOTELY CONTROLLED SUNRISE AND SUNSET MULTIMODES

CROSS-REFERENCE TO RELATED APPLICATIONS

This application is a divisional application of allowed application Ser. No. 15/447,191 filed Mar. 2, 2017, now U.S. Pat. No. 10,449,326, which claims benefit of priority to U.S. provisional application Ser. No. 62/302,858 filed Mar. 3, 2016 each of which is of the same inventive entity as herein and each incorporated herein by reference in its entirety.

FIELD OF THE INVENTION

This invention is drawn to the field of sleep or relaxation inducing or awaking or wakefulness therapy devices, more particularly, to a remotely programmable sleep and wake eye mask, and still more particularly, to a novel audio tone programmed hygienic and therapeutic sleep and wake eye mask having remotely controlled sunrise and sunset multimodes.

BACKGROUND OF THE INVENTION

Maintaining the wholeness and wholesomeness of the sleep/wake cycle day-to-day and month-to-month is essential to preserve personal well-being and happiness as well as the productivity and good order of society at large. In an ideal world, the rhythm of the sleep/wake cycle would be governed by the natural order of each days sunrise and sunset. The artificial routines of modern personal and social life, however, have eclipsed the rhythms of nature making it the more difficult to wake up and go to sleep at appointed times the more the exigencies of one's own routines are in conflict with the natural cycle of things.

A variety of devices have been devised in the effort to control the fundamental sleep and wake rhythms of the sleep/wake cycle in the face of the irregularities imposed thereon by the demands of modern life. Representative of such devices are the Sunrise Simulation Sleep Mask of United States patent application publication 2012/0137406 to Hide, dated Jun. 7, 2012; the Programmable Mask for Waking An individual of United States patent application publication 2007/0002692 to Van Brunt, dated Jan. 4, 2007; and the Relaxation Inducing Sleep Mask of U.S. Pat. No. 8,852,073 to Genereux et al., dated Oct. 7, 2014, each incorporated herein by reference. Reference in this connection may also be had to the Neuroon Intelligent Sleep Mask having a removable "smart pack," commercially available at https://neuroon.com.

The Hide and Van Brunt devices include a sleep mask having white LEDs and a controller cooperative therewith to wake the user in the morning with a rising, time-phased increase in intensity of white light. The controller can be a component integrally built into the mask and/or connected to the mask via a Bluetooth link. The Neuroon Intelligent Sleep Mask has a wake-up sunrise sequence and includes a Bluetooth connection to a mobile phone application used to determine control parameters, and provides different biometric sensors that are used to collect data on sleep time and states. A brightening sequence to provide controlled awakening from a nap is also disclosed by the Napwell Eye Mask Napping System, commercially available at http://napwell.com.

The heretofore known devices and techniques, however, have been disadvantageous in one or more of the following particulars. The cost has not been desirably low enough, due to the cost incurred by inclusion of time and alarm displays and multiple time and alarm set buttons and switches and costly electronics modules and Bluetooth communication interfaces, which has pushed their availability beyond the bounds of affordability for many consumers; the wake-up and go-to-sleep techniques employed thereby have not been entirely effective to simulate the sunrises and sunsets of nature, which has limited their ability to assimilate the sleep/wake cycle to the natural order and rhythms of nature; they have been uncomfortable to wear, or too heavy or cumbersome to use; and/or the utility of the heretofore known eye masks has been limited by the fact that once they became soiled during use, it is not been generally possible to maintain hygiene beyond superficial cleaning, which sometimes required a replacement product be acquired or the compromise made to continue to use sometimes even badly soiled eye masks.

SUMMARY OF THE INVENTION

One object of the present invention is to provide low-cost therapeutic sleep and wake eye masks.

This object is accomplished by the present invention by employing one control button and a low-cost programmable tone generator and tone communication protocol thereby eliminating costly time and alarm displays and Bluetooth communication interfaces.

Another object of the present invention is to make the therapeutic sleep and wake eye mask itself hygienic and readily cleanable.

This object is accomplished by the present invention by means of a mask assembly including a replaceable and/or washable or otherwise cleanable cover subassembly and an electro-optical core subassembly that is removably inserted therewithin. When soiled, the cover subassembly may be removed and cleaned or replaced with another cover subassembly if it were too soiled to be cleaned. This feature among others also allows for the advantage of replacement of cover subassemblies for purposes other than hygiene, such as to make a fashion statement or to select a cover subassembly that is finished to a different comfort or material grade.

A further object of the present invention is to disclose a therapeutic sleep and wake eye mask that provides simulated sunrise and sunset multimodes to assimilate the sleep/wake cycle to the natural rhythm of the day/night cycle. This object is accomplished by the present invention by means of an electro-optical core subassembly including an electronics module and full-spectrum red, green and blue LED light panels cooperative to provide full-spectrum light fields of intensity sufficient to be biologically effective of blue- and red-shifted spectra confronting the eyes when the mask is worn about the head respectively to simulate sunrise and sunset in different user selectable sunrise and sunset multimodes. Although red, green and blue LED panels are presently preferred, other means to provide full-spectrum cavity illumination in blue-shifted sunrise and red-shifted sunset multimodes could be employed.

In one disclosed sunrise mode, the electro-optical core subassembly is operative to illuminate the eyes with a biologically effective sunrise light field with blue spectral components simulating a natural sunrise of increasing magnitude starting at a time and lasting for a duration that corresponds to a desired wake-up time sequence.

In another disclosed sunrise mode, the electro-optical core subassembly is operative to illuminate the eyes with a biologically effective sunrise light field with blue spectral components simulating a natural sunrise of increasing magnitude that repetitively oscillates with a constant period corresponding to the brainwave frequency of someone who is waking up or is awake or is alert starting at a time and lasting for a duration that corresponds to a desired wake-up time sequence.

In a further disclosed sunrise mode, the electro-optical core subassembly is operative to illuminate the eyes with a biologically effective sunrise light field with blue spectral components simulating a natural sunrise of increasing magnitude that repetitively oscillates with a progressively decreasing period that sequentially corresponds to the brainwave frequency of someone who is waking up to someone who is awake or alert starting at a time and lasting for a duration that corresponds to a desired wake-up time sequence.

In one disclosed sunset mode, the electro-optical core subassembly is operative to illuminate the eyes with a biologically effective sunset light field with red spectral components simulating a natural sunset of decreasing magnitude starting at a time and lasting for a duration that corresponds to a desired sleep sequence.

In another disclosed sunset mode, the electro-optical core subassembly is operative to illuminate the eyes with a biologically effective sunset light field with red spectral components simulating a natural sunset of decreasing magnitude that repetitively oscillates with a constant period corresponding to the brainwave frequency of someone who is relaxed or is asleep starting at a time and lasting for a duration that corresponds to a desired sleep sequence.

In another disclosed sunset mode, the electro-optical core subassembly is operative to illuminate the eyes with a biologically effective sunset light field with red spectral components simulating a natural sunset of decreasing magnitude that repetitively oscillates with a progressively increasing period that sequentially corresponds to the brainwave frequency of someone who is relaxed to someone who is asleep starting at a time and lasting for a duration that corresponds to a desired sleep sequence.

In any sunrise and sunset mode having constant and variable period light fields, after the passage of a certain time interval, the brainwave frequencies of the user will become more and more entrained to the frequencies of the corresponding illumination oscillations, with the result that at some time the desired state will be synergistically induced.

A related object is to disclose a remotely programmable therapeutic sleep and wake eye mask having remotely controlled sunrise and sunset multimodes. This object is accomplished in accord with the present invention by setting mode and control times and other parameters of the processor of the electronics module of the electro-optical core subassembly according to control information input that is remotely entered to the UI of the low-cost tone control generator.

Other modes in different embodiments are contemplated including an afternoon energy boost mode and a circadian rhythm resetting mode.

BRIEF DESCRIPTION OF THE DRAWINGS

These and other inventive aspects, objects and advantageous features of the present invention will become more apparent as the invention becomes better understood by referring to the following, solely exemplary, detailed description of the presently preferred embodiments thereof, and to the drawings, wherein.

DETAILED DESCRIPTION OF THE PRESENTLY PREFERRED EMBODIMENTS

Figure 1:
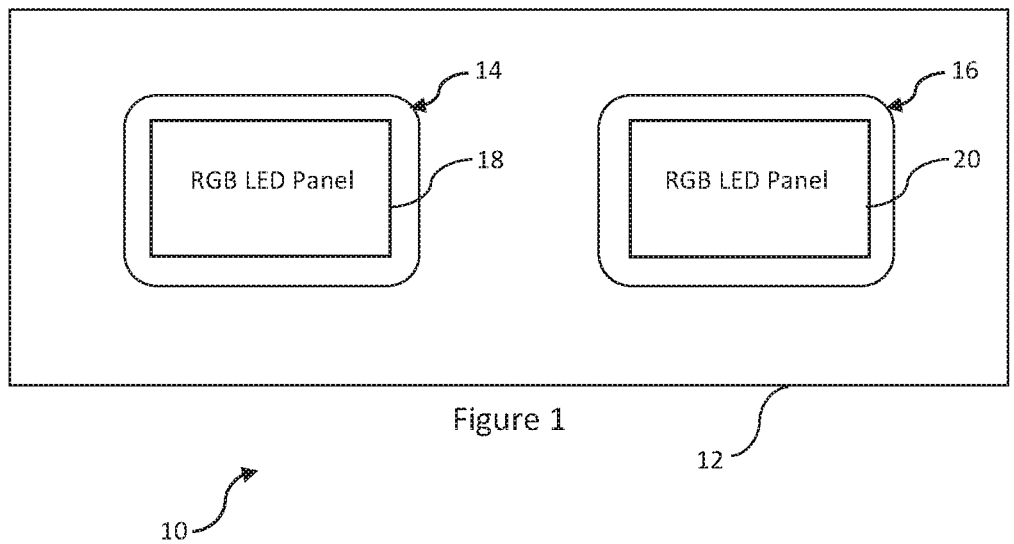
FIG. 1 is a schematic diagram of an eye mask of the audio tone programmed hygienic and therapeutic sleep and wake eye mask having remotely controlled sunrise and sunset multimodes of the present invention.

Referring now to FIG. 1, generally designated at 10 is an eye mask of the audio tone programmed hygienic and therapeutic sleep and wake eye mask having remotely controlled sunrise and sunset multimodes of the present invention. The eye mask 10 includes a member 12 adapted to be worn about the head and to comfortably seat against the face over the eyes of a wearer, not shown. The face-and-over-the-eyes-fitting member 12 of the eye mask 10 includes walls defining light-tight left and right eye cavities generally designated 14, 16 and full-spectrum red, green and blue LED panels 18, 20 mounted in the left and right eye cavities 14, 16 in position to illuminate the eyes, not shown, of the wearer. The mask is intended to be used with the user's eyes closed and the illumination provided in each of the sunrise and sunset multimodes to be described creates a subtle backlight through the eyelids.

In one presently preferred embodiment, each panel includes one red, one green, and one blue LED. As will be readily appreciated, when the red, green and blue LEDs of the red, green and blue LED panels 18, 20 are simultaneously illuminated, full-spectrum white light would result.

The face-and-over-the-eyes-fitting member 12 and the walls defining the left and right eye cavities 14, 16 of the eye mask 10 may be fashioned of any suitable flexible material comfortable enough to be worn about the head of a user. Although walls 14, 16 providing left and right eye cavities and red, green and blue LED light panels 18 and 20 to provide full-spectrum light fields in the left and right eye cavities are presently preferred, it will be appreciated that the walls defining the eye cavities can be differently configured, such as a single cavity common to both eyes, and/or a different full-spectrum source of biologically effective light fields having blue and red spectral components than that of the presently preferred embodiment, such as an array of one or more different point sources of white and/or colored light, or a single source visible to both eyes, that may include direct or indirect or backlit illumination, or color filters, among other ways to provide full-spectrum illumination and/or blue- and red-shifted illumination known to those of skill in the art can be employed.

Figure 2A:
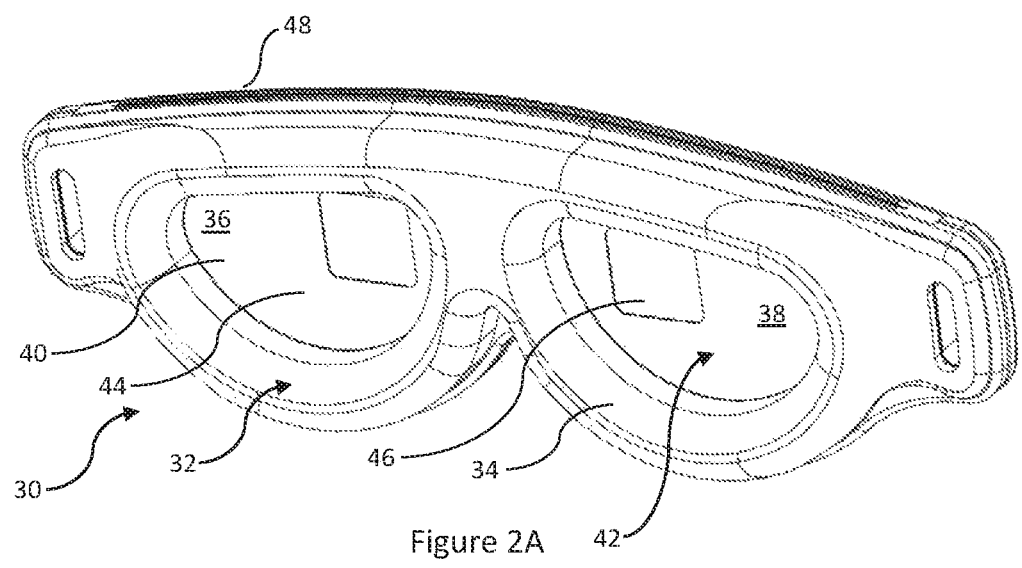
FIG. 2 is a pictorial view illustrating in the FIG. 2A thereof the proximate face of one presently preferred embodiment of an eye mask in accord with the present invention, illustrating in the FIG. 2B thereof an exploded pictorial view thereof showing an electro-optical core subassembly removed from but insertable within a cover subassembly adapted to be worn about the head and to comfortably seat on the face and illustrating in the FIG. 2C thereof an exploded pictorial view of the electro-optical core subassembly of the audio tone programmed hygienic and therapeutic sleep and wake eye mask having remotely controlled sunrise and sunset multimodes of the present invention.

Referring now to FIG. 2A, generally designated at 30 is a pictorial view of the proximate face of one presently preferred embodiment of an eye mask in accord with the audio tone programmed hygienic and therapeutic sleep and wake eye mask having remotely controlled sunrise and sunset multimodes of the present invention. The eye mask 30 includes a cover subassembly generally designated 32 including a first front portion 34 of soft, flexible material fashioned to include walls defining openings generally designated 36, 38 respectively confronting the left and right eyes of the user, and a second back portion 40 of flexible opaque material.

The portions 34, 40 of the cover subassembly 32 provide an electro-optical core subassembly receiving chamber within the eye mask 30, not shown, and an electro-optical core subassembly generally designated 42 including an electronics module, and red, green and blue LED panels 44, 46, is received within the cover subassembly 32 such that the left eye cavity 36 is illuminated by the red, green and blue LED panel 44 and the right eye cavity 38 is illuminated by the red, green and blue LED panel 46. As will be readily appreciated, a zipper mechanism 48 that releasably joins the top edges of the portions 34, 40 provides access to the electro-optical core subassembly receiving chamber and the electro-optical core subassembly received therewithin.

Although a pocket formed in the mask to removably receive the electro-optical subassembly is presently preferred, as is a zipper to releasably retain the same within the mask, it will be appreciated that other means than a pocket and cooperative zipper may be employed to removably insert the electro-optical subassembly within the cover subassembly allowing removal of the electro-optical core subassembly from a soiled cover subassembly and reinsertion of the same or another electro-optical subassembly in a cleaned or replacement cover subassembly without departing from the inventive concepts.

Figure 2B:
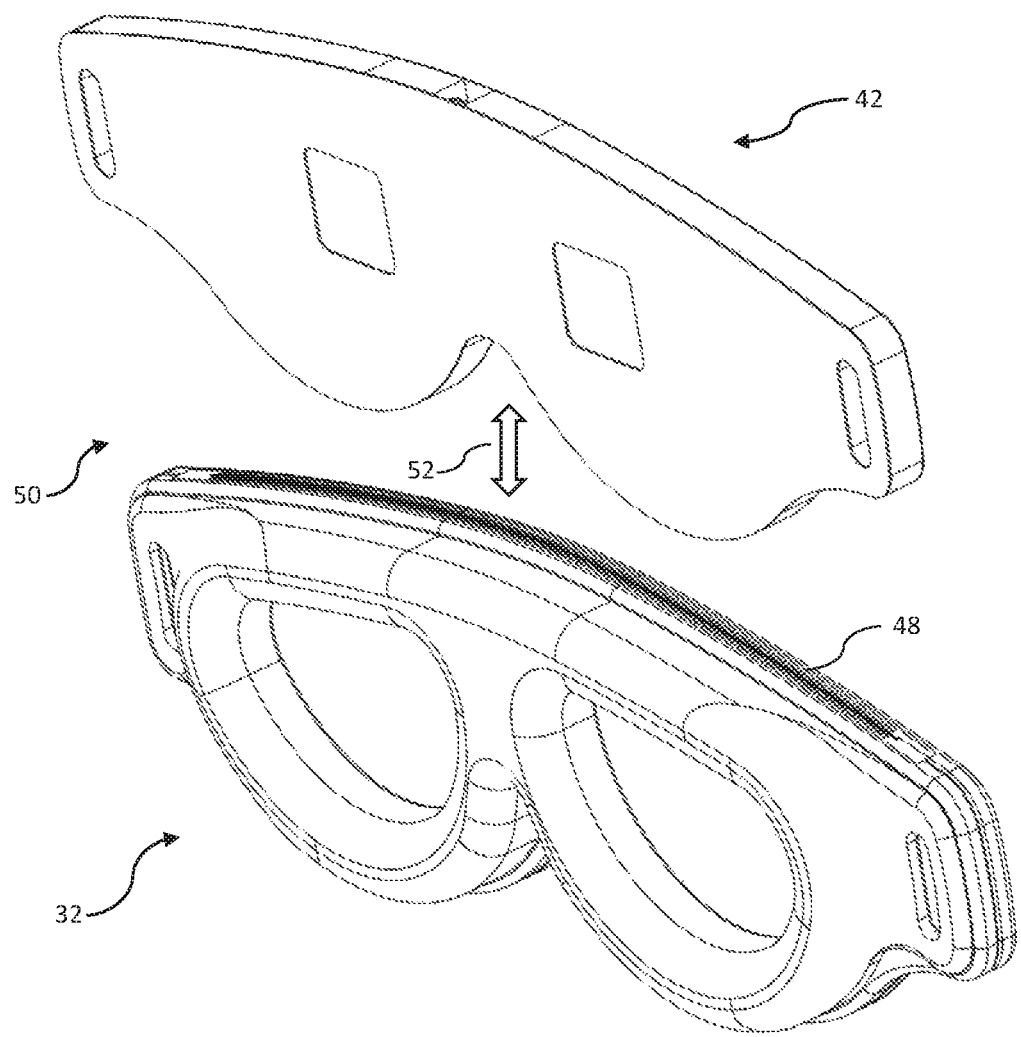

Referring now to FIG. 2B, generally designated at 50 is an exploded pictorial view of the eye mask of the audio tone programmed hygienic and therapeutic sleep and wake eye mask having remotely controlled sunrise and sunset multimodes of the present invention. As illustrated by arrow 52, the electro-optical core subassembly 42 is removably insertable within the cover subassembly 32 of the eye mask 30 via the zipper mechanism 48. As will be readily appreciated, the cover subassembly 32 in this manner may be replaced or readily cleaned when soiled and or interchanged for hygienic or other purposes such as by cover subassemblies having different fashion finishes or comfort or material grades. As will also be readily appreciated, different electro-optical core subassemblies can be swapped out as necessary or when desired to provide the same or another mode of programmed operation.

Figure 2C:
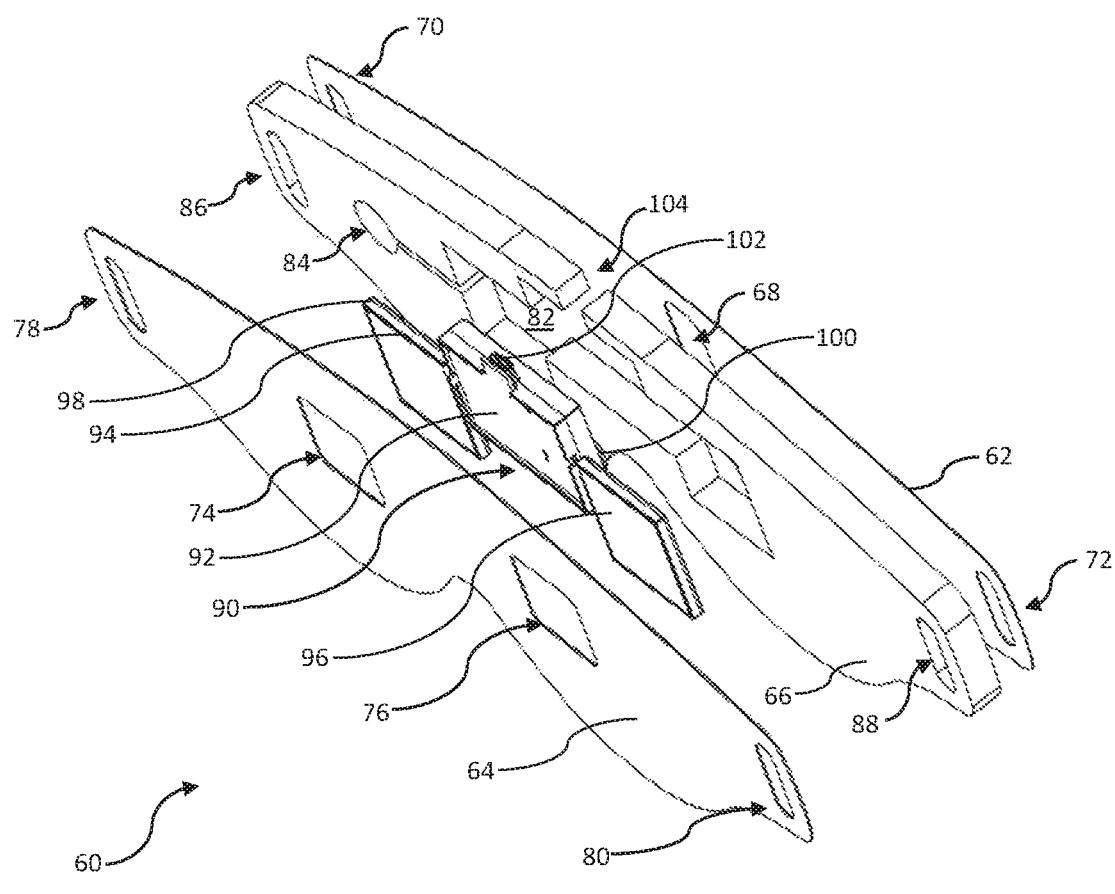

Referring now to FIG. 2C, generally designated at 60 is an exploded pictorial view of the electro-optical core subassembly of the audio tone programmed hygienic and therapeutic sleep and wake eye mask having remotely controlled sunrise and sunset multimodes of the present invention. The electro-optical core subassembly 60 includes distal and proximal layers 62, 64 of light blocking material such as black cloth and an intermediate layer 66 of foam or other comfortable or compressible material adhesively fastened therebetween. The layer 62 includes a cutout generally designated 68 intermediate it ends exposing a button and microphone, not shown, and cutouts generally designated 70, 72 proximate it ends. The layer 64 includes cutouts generally designated 74, 76 in spaced apart relation intermediate it ends and cutouts generally designated 78, 80 proximate it ends. The intermediate layer 66 is provided with an opening generally designated 82 to receive an electro-optical module and an opening generally designated 84 to receive a Piezo buzzer, not shown, that are intermediate it ends and cutouts generally designated 86, 88 proximate it ends. An electro-optical module generally designated 90 having an electronics module 92 to be described and left and right full-spectrum red, green and blue LED panels 94, 96 is inserted in the opening 82 provided therefor in the intermediate layer 66. A holder 98 peripherally captures the electronics module 86 and LED panels 90, 92 allowing for the insertion of the electro-optical module 90 as a unit into the opening 82 provided therefor in the intermediate layer 66. A button 100 is carried by distal surface of the electronics module 92. A USB port 102 is carried at the top of the electronics module 92 that faces upwardly and is made externally accessible by a channel generally designated 104 provided therefor in the intermediate member 66. As will be readily appreciated, a head strap, not shown, is releasably mounted to the aligned openings 70, 78, 86 and 72, 80, 88, although other strap or head attachment means could be employed.

As will be appreciated, sleep masks of another construction, such as those shown in U.S. Pat. No. 8,852,073, incorporated herein by reference, may be employed.

Figure 3:
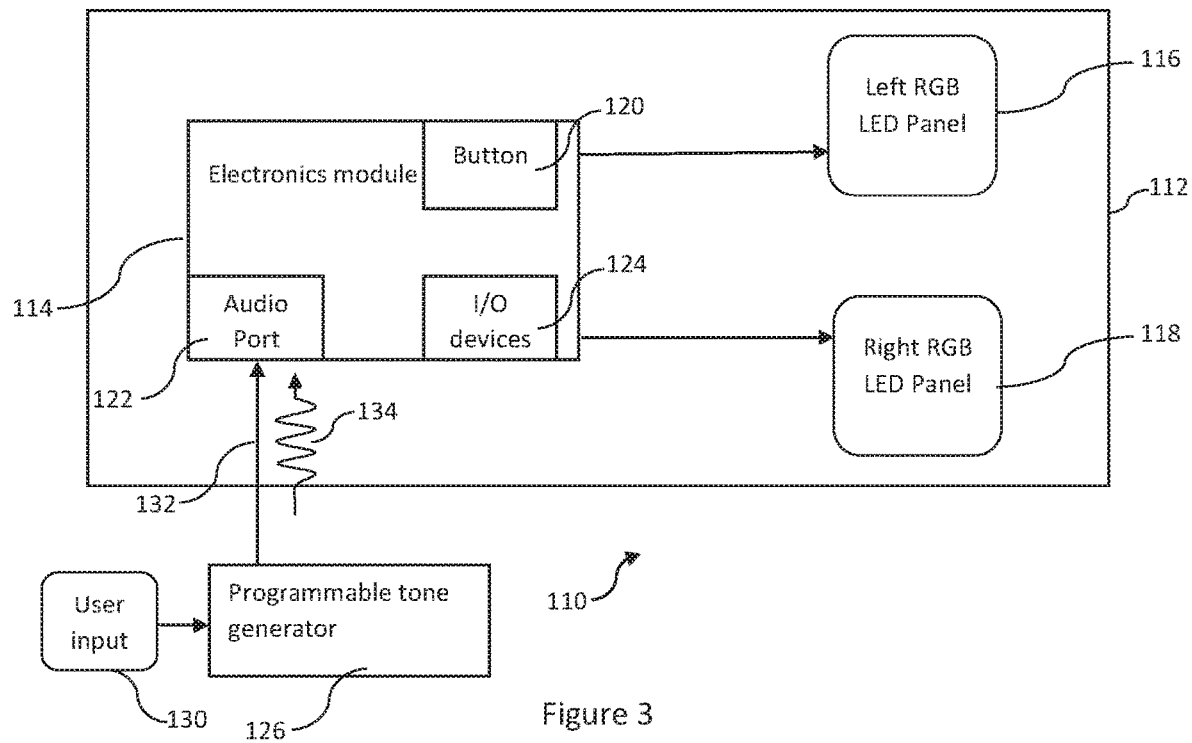
FIG. 3 is a schematic block diagram of the circuitry of one presently preferred embodiment of the audio tone programmed hygienic and therapeutic sleep and wake eye mask having remotely controlled sunrise and sunset multimodes of the present invention.

Referring now to FIG. 3, generally designated at 110 is a schematic block diagram of the circuitry of one presently preferred embodiment of the audio tone programmed hygienic and therapeutic sleep and wake eye mask having remotely controlled sunrise and sunset multimodes of the present invention. The electro-optical module is schematically illustrated by box 112 that includes an electronics module 114 including a controller and program and data memory, each not shown, well known to those of skill in the art. Left and right full-spectrum red, green and blue LED panels 116, 118 are operatively connected to the electronics module 114. In different sunrise and sunset multimodes to be described, the electronics module 114 and full-spectrum red, green and blue LED panels 116, 118 are cooperative to provide sunrise light fields with blue spectral components of increasing magnitude in any sunrise multimode selected to simulate a natural sunrise and to provide sunset light fields with red spectral components of decreasing magnitude to simulate a natural sunset in any sunset multimode selected. So long as the intensities are above biologically effective thresholds, the full-spectrum light fields with blue-shifted spectra of increasing magnitude signal the brain that the sun has risen and the body should prepare for daytime and the full-spectrum light fields with red-shifted spectra of decreasing magnitude signal the brain that the sun is setting and the body should prepare for evening and sleep. Any suitably blue-shifted illumination with intensity distribution of the cavity illumination intensified around the blue region of the spectra, such as four hundred fifty (450) nm to four hundred ninety-five (495) nm, so that the illumination appearing therein is substantially and predominantly "blue," could be employed. Any suitably red-shifted illumination with intensity distribution of the cavity illumination intensified around the red region of the spectra, such as six hundred twenty (620) nm, to seven hundred fifty (750) nm, so that the illumination appearing therein is substantially and predominantly "red," could be employed. A control button 120, an audio port 122 and I/O devices 124 including a Piezo buzzer and REM sensor are operatively connected to the controller of the electronics module 114. The Piezo buzzer is provided to produce alarm sounds at desired times.

A programmable tone generator 126 is connected to the audio port 122 so as to provide a communication interface therebetween. The programmable tone generator 122, that is remote from the electro-optical module 112, includes a UI (user interface) and is used as a remote to control the processor of the electronics module 114 in accord with user input mode and control parameter selection as schematically illustrated by box 130. Any device with a controller, web browser and an audio output can provide tone programming. The programmable tone generator may also be a hand-held, dedicated, tone control device. Preferably, the programmable tone generator 126 is an application adapted for use on an Android smartphone, iPhone, PC or other web enabled devices. Although a programmable tone controller is presently preferred, the remote control function of setting illumination mode and operational parameters could be implemented by other communication devices and methods, such as Bluetooth communication protocol, in alternate remote control embodiments contemplated herein.

In different disclosed embodiments, the audio port 122 may be a microphone and a USB port.

Figure 4:
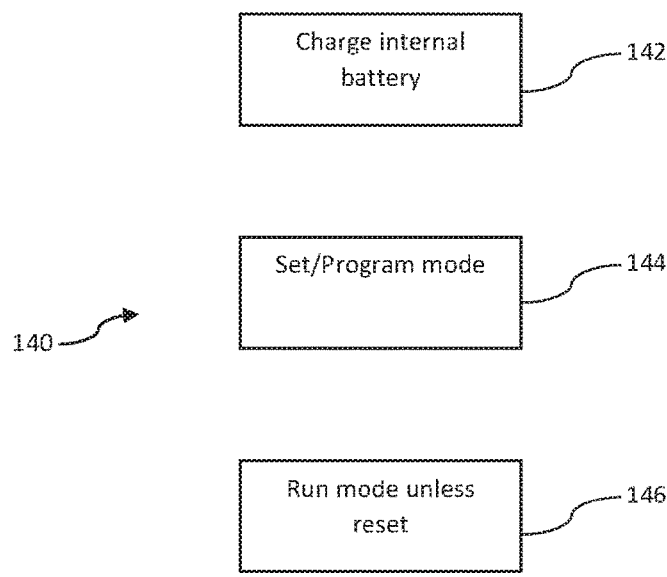
FIG. 4 is a state diagram of the processor of electronics module of the electro-optical core subassembly of the audio tone programmed hygienic and therapeutic sleep and wake eye mask having remotely controlled sunrise and sunset multimodes of the present invention.

Referring now to FIG. 4, generally designated at 140 is a state diagram of the controller of the electronics module of the electro-optical module of the audio tone programmed hygienic and therapeutic sleep and wake eye mask having remotely controlled sunrise and sunset multimodes of the present invention.

In charge internal battery state schematically illustrated by box 142, the controller is operative to charge its internal battery, not shown, when connected to electrical power, not shown.

The set/program state is schematically illustrated by box 144. The programmable tone generator application 126 is opened by the user and its UI is used to remotely set the controller of the electronics module of the electro-optical core subassembly for operation in a selected one of the sunrise and sunset multimodes of the present invention. The UI of the programmable tone generator 126 displays fields, not shown, to allow the user to select the alarm time, to select the desired duration of the sunrise light sequence, the desired duration of the sunset light sequence, to select one of the sunrise multimodes to be described and among others to select one of the sunset multimodes to be described. The tone generator 126 is programmed to generate a uniquely coded tone sequence to be described to the electronics module 114 via USB cable 132, when the audio port 122 is a USB port, and as an audible tone sequence schematically illustrated by wavy arrow 134, when the audio port 122 is a microphone. In response to a long press of the button 120, the controller of the electronics module 114 enters set/program state 144 and is operative in response to receipt of the uniquely coded tone sequence to set its program mode and sequence parameters in accord therewith.

In run mode unless reset state schematically illustrated by box 146, the controller is operative to run the mode selected at any times designated until it is reset to another mode or a manual override is input via the button 120 (FIG. 3).

With reference to FIG. 5, the sunrise multimodes simulating a natural sunrise to assimilate the wake phase of the sleep/wake cycle to the day phase of the natural rhythm of day and night of the audio tone programmed hygienic and therapeutic sleep and wake eye mask having remotely controlled sunrise and sunset multimodes of the present invention will now be described. By sunrise light field illumination is meant light fields produced by the eye mask's electro-optical module of the electro-optical core subassembly so as to illuminate the eyes of the wearer with blue spectral components simulating a natural sunrise of physiologically effective intensity in any sunrise mode selected.

Figure 5A:
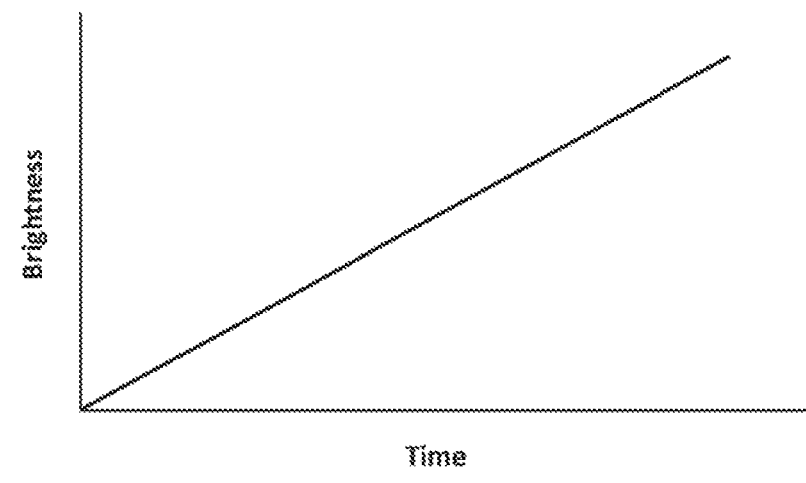
FIG. 5 illustrates in the FIGURE SA-5C thereof graphs of intra-cavity light magnitude with time useful in explaining the principles of the sunrise multimodes with biologically effective blue spectral components simulating a natural sunrise of the audio tone programmed hygienic and therapeutic sleep and wake eye mask having remotely controlled sunrise and sunset multimodes of the present invention.

Referring now to FIG. 5A, generally designated at 150 is a graph of the brightness of sunrise light field illumination with time in one sunrise mode in accord with the present invention. In the sunrise mode 150, the brightness of sunrise light field illumination with blue spectral components simulating a natural sunrise is shown increasing in magnitude, starting at a time and lasting for a duration that corresponds to a desired wake-up time sequence. For example, a typical wake-up time sequence would be ten (10) minutes of increasing blue-shifted light in a first time interval to signal daybreak followed by a second interval of white light, not shown, to signal the light of the fully risen sun; thereafter, cavity illumination is turned off.

Figure 5B:
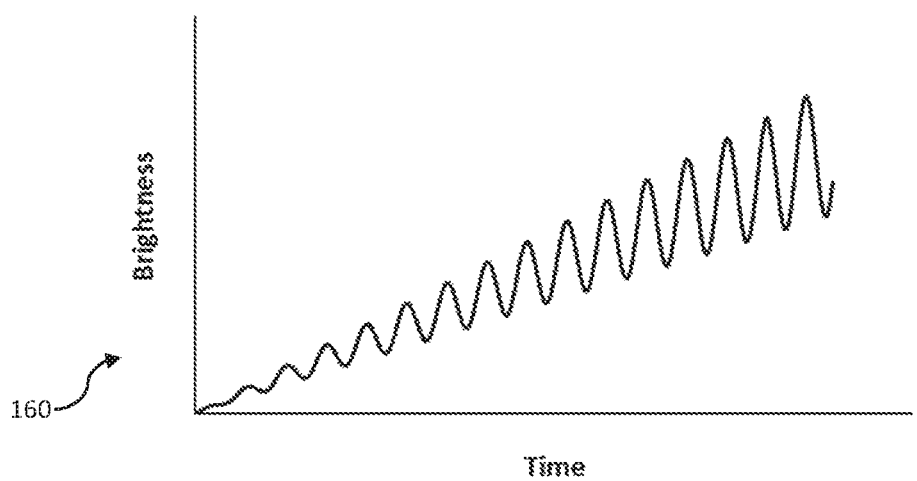

Referring now to FIG. 5B, generally designated at 160 is a graph of the brightness of sunrise light field illumination with time in another sunrise mode in accord with the present invention. In the sunrise mode 160, the brightness of sunrise light field illumination with blue spectral components simulating a natural sunrise is shown increasing in magnitude and oscillating with a constant period corresponding to the brainwave frequency of someone who is waking up or is awake or is alert, starting at a time and lasting for a duration that corresponds to a desired wake-up time sequence. For example, the oscillations may occur at high Delta to guide the user from a deep sleep into a light sleep and an awakened state. The mind will slowly synchronize with the stimuli it is presented with. Presenting a frequency which is higher than the current state will encourage the mind or brain into the state associated with the higher frequency.

Figure 5C:
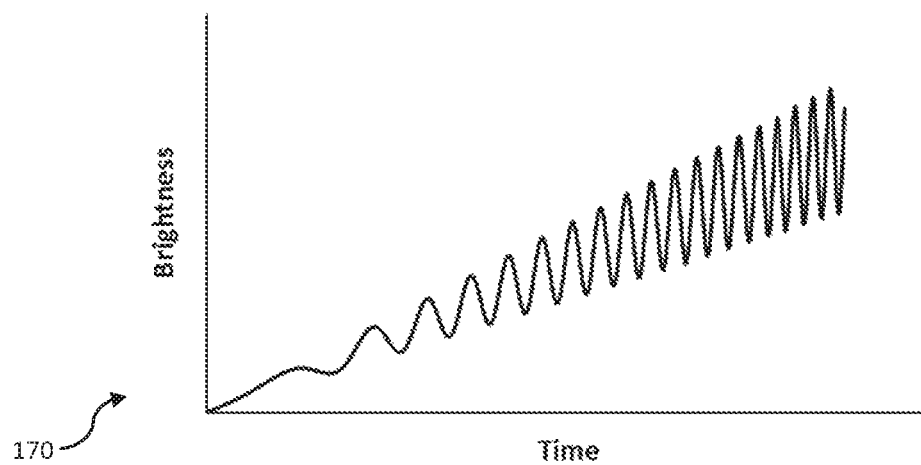

Referring now to FIG. 5C, generally designated at 170 is a graph of the brightness of sunrise light field with time in another sunrise mode in accord with the present invention. In the sunrise mode 170, the brightness of sunrise light field illumination with blue spectral components simulating a natural sunrise is shown increasing in magnitude and oscillating with a decreasing period in sequence respectively to the brainwave frequencies of someone who is asleep to someone who is awake or is alert, starting at a time and lasting for a duration that corresponds to a desired wake-up time sequence. For example, the oscillations may begin in low Delta and speed up into high Delta to ease the user out of deep sleep.

With reference to FIG. 6, the sunset multimodes simulating a natural sunset to assimilate the sleep phase of the sleep/wake cycle to the night phase of the natural rhythm of day and night of the audio tone programmed hygienic and therapeutic sleep and wake eye mask having remotely controlled sunrise and sunset multimodes of the present invention will now be described. By sunset light field illumination is meant light fields produced by the eye mask's electro-optical module of the electro-optical core subassembly so as to illuminate the eyes of the wearer with red spectral components simulating a natural sunset of physiologically effective intensity in any sunset mode selected.

Figure 6A:
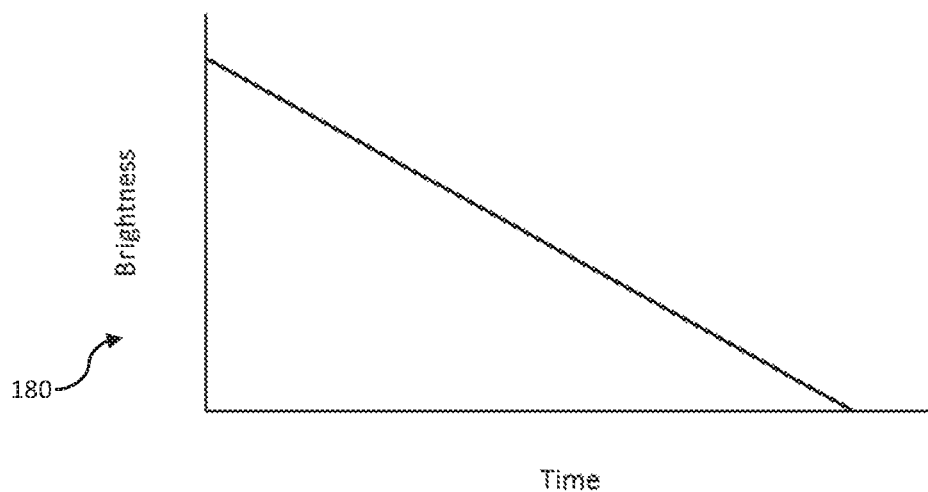
FIG. 6 illustrates in the FIGS. 6A-6C thereof graphs of intra-cavity light magnitude with time useful in explaining the principles of the sunset multimodes with biologically effective red spectral components simulating a natural sunset of the audio tone programmed hygienic and therapeutic sleep and wake eye mask having remotely controlled sunrise and sunset multimodes in accord with the present invention.

Referring now to FIG. 6A, generally designated at 180 is a graph of the brightness of sunrise light field illumination with time in one sunset mode in accord with the present invention. In the sunset mode 180, the brightness of sunset light field illumination with red spectral components simulating a natural sunset is shown decreasing in magnitude, starting at a time that begins by a short depression of the button 120 (FIG. 3) and lasting for a duration that corresponds to a desired sunset sequence. For example, a typical sleep sequence would be ten (10) minutes of decreasing red-shifted light to signal that the sun has set followed by complete darkness to signal nightfall. It is noted that the brightness of the red-shifted illumination can be manually adjusted by long depression of the button 120 (FIG. 3).

Figure 6B:
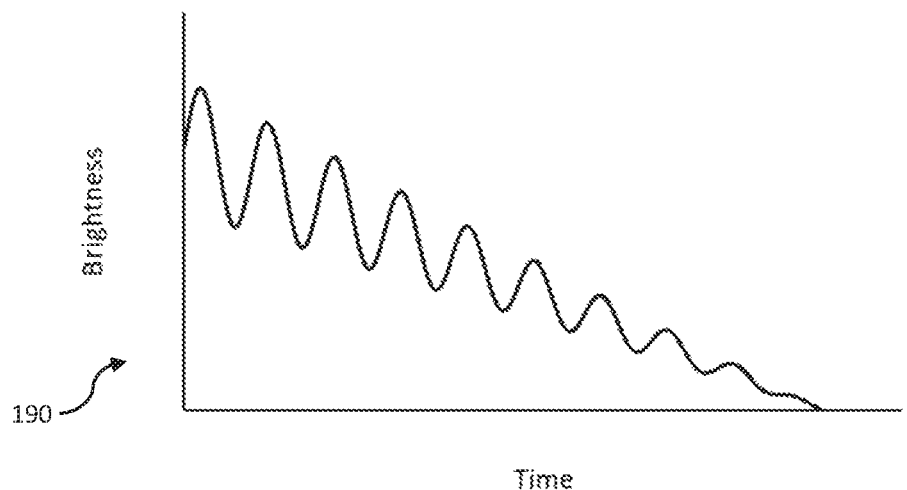

Referring now to FIG. 6B, generally designated at 190 is a graph of the brightness of sunset light field illumination with time in another sunset mode in accord with the present invention. In the sunset mode 190, the brightness of sunset light field illumination with red spectral components simulating a natural sunset is shown decreasing in magnitude and oscillating with a constant period corresponding to the brainwave frequency of someone who is relaxed or is asleep, starting at a time initiated by short pressing the button 120 (FIG. 3) and lasting for a duration that corresponds to a desired sleep sequence. For example, the oscillations may occur at low Delta to guide the user from a wakeful or relaxed state to a state of deeper relaxation and sleep.

Figure 6C:
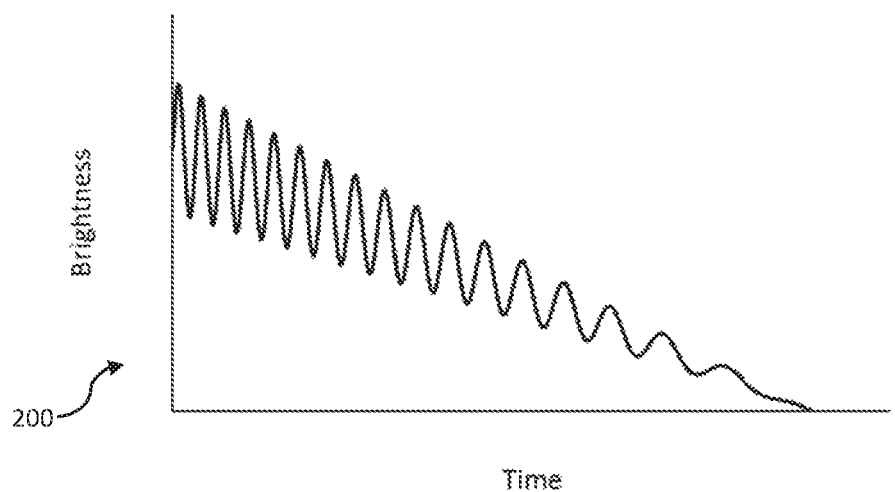

Referring now to FIG. 6C, generally designated at 200 is a graph of the brightness of sunset light field with time in another sunset mode in accord with the present invention. In the sunset mode 200, the brightness of sunset light field illumination with red spectral components simulating a natural sunset is shown decreasing in magnitude and oscillating with an increasing period corresponding in sequence respectively to the brainwave frequencies of someone who is relaxed to someone who is asleep, starting at a time initiated by short pressing the button 120 (FIG. 3) and lasting for a duration that corresponds to a desired sleep sequence. For example, the oscillations may begin in high Delta (4 Hz) slowing to low Delta (0.5 Hz) to induce relaxation and sleep.

In any sunset mode, the sunset illumination can be canceled by short pressing the button 120 (FIG. 3).

U.S. Pat. No. 8,638,950, entitled Digital Sound Relaxation and Sleep-inducing System and Method, dated Jan. 28, 2014, to Anderson et al., incorporated herein by reference, discloses among other things a processor-implemented sound controller operative to replay sound tracks at progressively slower replay rates in successive time intervals to synergistically co-act with the listener's biorhythms to induce a state of deep relaxation that helps the listener to fall asleep. In alternate embodiments, not shown, speakers coupled to the eye mask are provided and the controller of the electronics module of the electro-optical module is operatively coupled thereto and is programmed in different user selectable modes to provide sound therethrough in accord with U.S. Pat. No. 8,638,950 alone or in combination with sunset illumination. As will be appreciated, when in a programmed combination mode, the co-presence to the ears and eyes of the wearer of selected audio in accord with U.S. Pat. No. 8,638,950 and of red-shifted illumination provided by a selected sunset mode synergistically co-acts to promote rest and to induce sleep.

Figure 7:
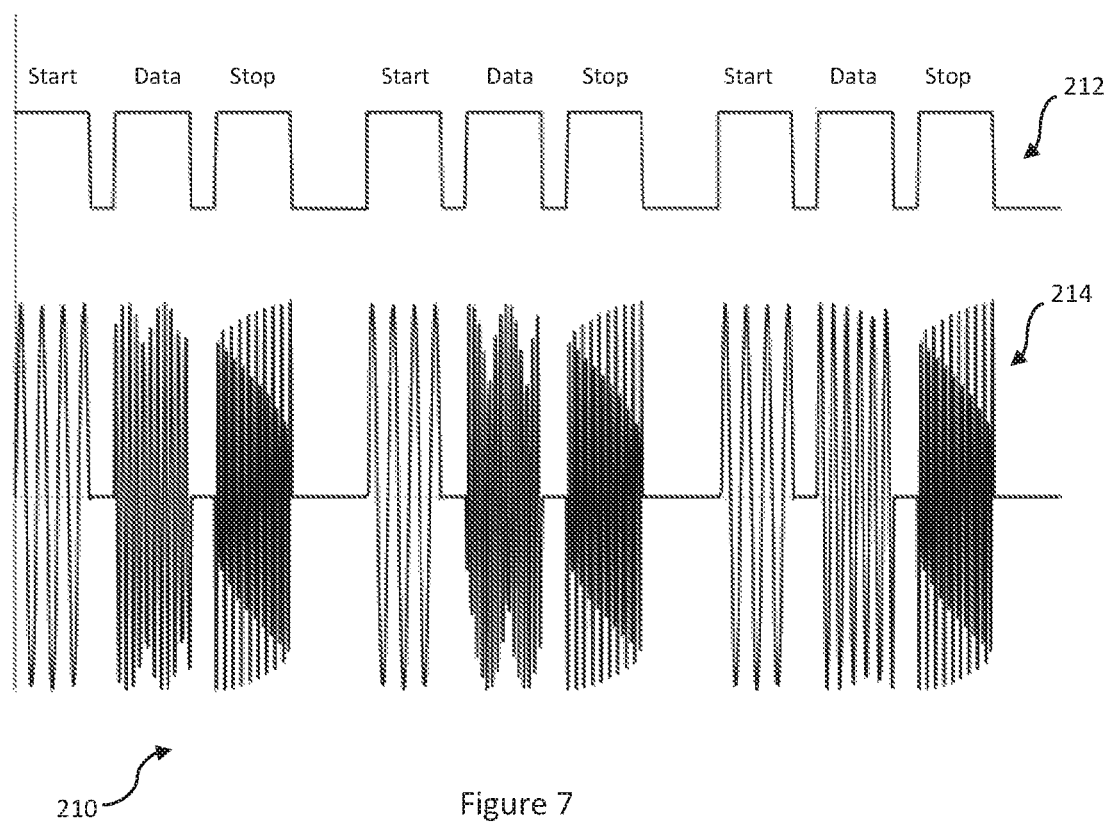
FIG. 7 is a diagram illustrating one presently preferred tone control protocol of the programmable tone generator of the audio tone programmed hygienic and therapeutic sleep and wake eye mask having remotely controlled sunrise and sunset multimodes of the present invention.

Referring now to FIG. 7, generally designated at 210 is a signal diagram illustrating one presently preferred tone control protocol implemented by the programmable tone generator of the audio tone programmed hygienic and therapeutic sleep and wake eye mask having remotely controlled sunrise and sunset multimodes of the present invention. As shown by sequence generally designated 212, the protocol preferably is implemented as a start tone, and a data tone followed by a stop tone. The audio tones corresponding thereto are generally designated 214. If shorter data streams and faster programming were desired, a space tone in between data tones could be employed.

One advantageous feature of the tone control protocol is that the length of the tone is not critical and does not even need to be consistent between tones. It is a sort of adaptive tone decoder and differentiates the tone control protocol from a serial connection which is very sensitive to timing. There are twelve (12) different frequencies representing zero (0) through nine (9) as well as start and stop. This allows to send four (4) bits of data with one tone set instead of having to encode the number that the tone represents with ones (1's) and zeros (0's). A checksum of the data to double check that the data is correct is employed.

In one presently preferred embodiment, the programmable tone control generator uses sound frequencies in the audible range between five hundred (500) Hz and two thousand (2000) Hz. It is understood that the same technique could apply to barely audible frequencies such as fifteen (15) kHz to twenty (20) kHz or beyond the range of human hearing (ultrasound) above twenty (20) kHz. This could allow for programming of the device with sound using a method that would be perceived to be silent by the user.

The preferred format is as follows, with each digit being a different frequency of sound being played, clock time, alarm time, option settings. An example would be clock time: 17:29 alarm time: 06:45 options: 1529. The options correspond to the different modes and other parameters that have been selected. For this example, 17:29 06:45 1529
|Start|1|Stop|Start|7|Stop|Start|2|Stop|Start|9|Stop|Start|0
|Stop|Start|6|Stop|Start|4|Stop|Start|5|Stop|Start|1|Stop
|Start|5|Stop|Start|2|Stop|Start|9|Stop|Start|Checksum|Stop
As mentioned above, this could be reduced to:
|Start|1|Start|7|Start|2|Start|9|Start|0|Start|6|Start|4|Start|5
|Start|1|Start|5|Start|2|Start|9|Start Checksum|Start
This is only to illustrate that it is not a fixed protocol.

It will be appreciated that the controlled information transmission of the programmable tone generator will have utility in other applications where there is the need for low cost effective information transfer between devices.

Many modifications and alternate embodiments of the various subassemblies and other modes are possible; for example, an energize mode to address one's mid-afternoon dip in energy is contemplated. In this energization mode, for example, the mask is put on and the electro-optical core subassembly activated for ten (10) minutes with blue light and excitation frequencies consistent with wakefulness. Another mode is a circadian rhythm reset mode. In this mode, the mask is put on and the electro-optical core assembly activated to provide white light that oscillates in magnitude with a period corresponding to frequencies known to affect resetting of the circadian rhythm of the wearer. Reference in this connection may be had to the article entitled "Temporal Integration of Light Flashes by the Human Circadian System," by Najjar and Zeitzer, appearing at the Journal of Clinical Investigation, Clin Invest. Doi: 1172/jc182306, dated December, 2015, incorporated herein by reference. In another mode, the processor of the electronics module of the electro-optical module is programmed to operate in response to information from REM sensor detection of the sleep or other brain state to awake the user at an optimum point within a morning wake-up interval. If the mask comes off, the lights can't wake the user in the morning. A solution for this is to use a larger light source located somewhere in the bedroom. A bed side lamp could in addition to or instead of a sleep and wake eye mask be employed; basically, instead of or in addition to illuminating the inside of a mask that the user wears, the room is illuminated with the bed side lamp or other full spectrum illumination source having blue-shifted and/or red-shifted spectra. The programming is the same, the light colors and pulsing are also the same, in these embodiments.

What is claimed is:

1. A therapeutic sleep and wake eye mask that provides simulated sunrise and sunset multimodes for a user having a sleep/wake cycle and subject to nature's day/night rhythmic cycle to assimilate the sleep/wake cycle to the natural rhythm of the day/night cycle, comprising:

a member adapted to be worn about a user's head and to seat against a user's face over a user's eyes that includes walls defining light-tight left and right eye cavities;

an electro-optical module carried by said member that includes an electronics module including a user input interface, a controller and a source of light cooperative to provide illumination of the left and right eye cavities in accord with user input sunrise and sunset mode selection and start time and sequence length selection;

wherein said mode selection is a sunrise mode that fills said left and right cavities with sunrise illumination that fills said left and right cavities with increasing magnitude light having blue-shifted spectra of physiologically effective intensity to simulate a natural sunrise that signals brain and body that the sun has risen and the body should prepare for daytime starting at a time and lasting for a duration that corresponds to a desired wake-up time sequence;

wherein said mode selection is a sunset mode that fills said left and right cavities with sunset illumination that fills said left and right cavities with decreasing magnitude light having red-shifted spectra of physiologically effective intensity to simulate a natural sunset that signals brain and body that the sun is setting and the body should prepare for evening and sleep lasting for a duration that corresponds to a desired sleep sequence; and wherein said sunrise illumination that fills said left and right cavities with increasing magnitude light having blue-shifted spectra oscillates with a constant period corresponding to the brainwave frequency of someone who is in a state of waking up or is awake or is alert, starting at a time and lasting for a duration that corresponds to a desired wake-up time sequence such that after the passage of a certain time interval, the brainwave frequencies of the user will become more and more entrained to the frequency of the corresponding illumination oscillations, with the result that at some time the state of waking up or being awake or being alert will be induced.

2. A therapeutic sleep and wake eye mask that provides simulated sunrise and sunset multimodes for a user having a sleep/wake cycle and subject to nature's day/night rhythmic cycle to assimilate the sleep/wake cycle to the natural rhythm of the day/night cycle, comprising:

a member adapted to be worn about a user's head and to seat against a user's face over a user's eyes that includes walls defining light-tight left and right eye cavities;

an electro-optical module carried by said member that includes an electronics module including a user input interface, a controller and a source of light cooperative to provide illumination of the left and right eye cavities in accord with user input sunrise and sunset mode selection and start time and sequence length selection;

wherein said mode selection is a sunrise mode that fills said left and right cavities with sunrise illumination that fills said left and right cavities with increasing magnitude light having blue-shifted spectra of physiologically effective intensity to simulate a natural sunrise that signals brain and body that the sun has risen and the body should prepare for daytime starting at a time and lasting for a duration that corresponds to a desired wake-up time sequence;

wherein said mode selection is a sunset mode that fills said left and right cavities with sunset illumination that fills said left and right cavities with decreasing magnitude light having red-shifted spectra of physiologically effective intensity to simulate a natural sunset that signals brain and body that the sun is setting and the body should prepare for evening and sleep lasting for a duration that corresponds to a desired sleep sequence; and wherein said sunrise illumination that fills said left and right cavities with increasing magnitude light having blue-shifted spectra oscillates with a decreasing period corresponding in sequence respectively to the brainwave frequencies of someone who is in an asleep state to someone who is in an awake or is in an alert state, starting at a time and lasting for a duration that corresponds to a desired wake-up time sequence such that after the passage of a certain time interval, the brainwave frequencies of the user will become more and more entrained to the frequencies of the corresponding illumination oscillations, with the result that at some time the states of being awake or being alert will be induced.

3. A therapeutic sleep and wake eye mask that provides simulated sunrise and sunset multimodes for a user having a sleep/wake cycle and subject to nature's day/night rhythmic cycle to assimilate the sleep/wake cycle to the natural rhythm of the day/night cycle, comprising:

a member adapted to be worn about a user's head and to seat against a user's face over a user's eyes that includes walls defining light-tight left and right eye cavities;

electro-optical module carried by said member that includes an electronics module including a user input interface, a controller and a source of light cooperative to provide illumination of the left and right eye cavities in accord with user input sunrise and sunset mode selection and start time and sequence length selection;

wherein said mode selection is a sunrise mode that fills said left and right cavities with sunrise illumination that fills said left and right cavities with increasing magnitude light having blue-shifted spectra of physiologically effective intensity to simulate a natural sunrise that signals brain and body that the sun has risen and the body should prepare for daytime starting at a time and lasting for a duration that corresponds to a desired wake-up time sequence;

wherein said mode selection is a sunset mode that fills said left and right cavities with sunset illumination that fills said left and right cavities with decreasing magnitude light having red-shifted spectra of physiologically effective intensity to simulate a natural sunset that signals brain and body that the sun is setting and the body should prepare for evening and sleep lasting for a duration that corresponds to a desired sleep sequence; and wherein said sunset illumination that fills said left and right cavities with decreasing magnitude light having red-shifted spectra oscillates with a constant period corresponding to the brainwave frequency of someone who is in a relaxed or is in an asleep state lasting for a duration that corresponds to a desired sleep sequence such that after the passage of a certain time interval, the brainwave frequencies of the user will become more and more entrained to the frequency of the corresponding illumination oscillations, with the result that at some time the relaxed or the asleep state will be induced.

4. A therapeutic sleep and wake eye mask that provides simulated sunrise and sunset multimodes for a user having a sleep/wake cycle and subject to nature's day/night rhythmic cycle to assimilate the sleep/wake cycle to the natural rhythm of the day/night cycle, comprising:

a member adapted to be worn about a user's head and to seat against a user's face over a user's eyes that includes walls defining light-tight left and right eye cavities;

an electro-optical module carried by said member that includes an electronics module including a user input interface, a controller and a source of light cooperative to provide illumination of the left and right eye cavities in accord with user input sunrise and sunset mode selection and start time and sequence length selection;

wherein said mode selection is a sunrise mode that fills said left and right cavities with sunrise illumination that fills said left and right cavities with increasing magnitude light having blue-shifted spectra of physiologically effective intensity to simulate a natural sunrise that signals brain and body that the sun has risen and the body should prepare for daytime starting at a time and lasting for a duration that corresponds to a desired wake-up time sequence;

wherein said mode selection is a sunset mode that fills said left and right cavities with sunset illumination that fills said left and right cavities with decreasing magnitude light having red-shifted spectra of physiologically effective intensity to simulate a natural sunset that signals brain and body that the sun is setting and the body should prepare for evening and sleep lasting for a duration that corresponds to a desired sleep sequence; and wherein said sunset illumination that fills said left and right cavities with decreasing magnitude light having red-shifted spectra oscillates with an increasing period corresponding in sequence respectively to the brainwave frequencies of someone who is in a relaxed state to someone who is in an asleep state, starting at a time and lasting for a duration that corresponds to a desired sleep sequence such that after the passage of a certain time interval, the brainwave frequencies of the user will become more and more entrained to the frequencies of the corresponding illumination oscillations, with the result that at some time the asleep state will be induced.

* * * * *